(12) United States Patent
Kiyan et al.

(10) Patent No.: US 10,653,389 B2
(45) Date of Patent: May 19, 2020

(54) ULTRASONIC DIAGNOSING DEVICE

(71) Applicant: Furuno Electric Co., Ltd., Nishinomiya (JP)

(72) Inventors: Wataru Kiyan, Nishinomiya (JP); Takeshi Kawajiri, Nishinomiya (JP); Mitsuhiko Hataya, Nishinomiya (JP)

(73) Assignee: Furuno Electric Co., Ltd., Nishinomiya (JP)

( * ) Notice: Subject to any disclaimer, the term of this patent is extended or adjusted under 35 U.S.C. 154(b) by 112 days.

(21) Appl. No.: 15/027,681

(22) PCT Filed: Sep. 2, 2014

(86) PCT No.: PCT/JP2014/073000
§ 371 (c)(1),
(2) Date: Apr. 6, 2016

(87) PCT Pub. No.: WO2015/053008
PCT Pub. Date: Apr. 16, 2015

(65) Prior Publication Data
US 2016/0242738 A1     Aug. 25, 2016

(30) Foreign Application Priority Data

Oct. 7, 2013    (JP) ................................. 2013-210184

(51) Int. Cl.
    *A61B 8/00*        (2006.01)
    *A61B 8/08*        (2006.01)
    *A61B 8/14*        (2006.01)

(52) U.S. Cl.
CPC ............ *A61B 8/4461* (2013.01); *A61B 8/085* (2013.01); *A61B 8/0858* (2013.01); *A61B 8/14* (2013.01); *A61B 8/4209* (2013.01); *A61B 8/4281* (2013.01)

(58) Field of Classification Search
None
See application file for complete search history.

(56) References Cited

U.S. PATENT DOCUMENTS

| | | | | |
|---|---|---|---|---|
| 4,059,098 A | * | 11/1977 | Murdock | ............. A61B 8/4281 |
| | | | | 600/437 |
| 4,084,582 A | * | 4/1978 | Nigam | ..................... A61B 8/00 |
| | | | | 367/150 |

(Continued)

FOREIGN PATENT DOCUMENTS

| CN | 101002690 A | 7/2007 |
|---|---|---|
| CN | 101427940 A | 5/2009 |

(Continued)

OTHER PUBLICATIONS

ISA Japanese Patent Office, International Search Report Issued in Application No. PCT/JP2014/073000, dated Oct. 7, 2014, WIPO, 4 pages.

*Primary Examiner* — Pascal M Bui Pho
*Assistant Examiner* — Farouk A Bruce
(74) *Attorney, Agent, or Firm* — Alleman Hall Creasman & Tuttle LLP

(57) ABSTRACT

An ultrasonic diagnosing device is provided for diagnosing a state of a to-be-examined part based on echo signals caused by ultrasonic signals. The device includes a container body containing liquid and capable of coming in close contact with a to-be-examined body, an ultrasonic wave penetrating part having ultrasonic penetrability and covering an opening formed in the container body, a probe having an ultrasonic wave transmitting part configured to transmit the ultrasonic signals, and a drive mechanism configured to move the probe inside the container body and change a position of the ultrasonic wave transmitting part. The probe being soaked in the liquid inside the container body in a state where the ultrasonic wave transmitting part is separated (Continued)

from the ultrasonic wave penetrating part, and the ultrasonic signals being transmitted to the to-be-examined body through the liquid and the ultrasonic wave penetrating part by the ultrasonic wave transmitting part.

8 Claims, 8 Drawing Sheets

(56) References Cited

U.S. PATENT DOCUMENTS

| | | | |
|---|---|---|---|
| 4,485,819 A | 12/1984 | Igl | |
| 5,140,988 A * | 8/1992 | Stouffer | A22B 5/007 |
| | | | 600/437 |
| 2004/0122322 A1* | 6/2004 | Moore | A61B 8/14 |
| | | | 600/459 |
| 2007/0044336 A1 | 3/2007 | Ilkubo et al. | |
| 2007/0239020 A1 | 10/2007 | Iinuma et al. | |
| 2008/0319318 A1* | 12/2008 | Johnson | A61B 8/0825 |
| | | | 600/445 |
| 2010/0063396 A1* | 3/2010 | Anderson | A61B 8/0825 |
| | | | 600/459 |
| 2011/0126629 A1* | 6/2011 | Nakamura | A61B 8/0858 |
| | | | 73/644 |
| 2011/0301461 A1 | 12/2011 | Anite | |
| 2013/0237826 A1* | 9/2013 | Levien | A61B 8/4281 |
| | | | 600/448 |

FOREIGN PATENT DOCUMENTS

| | | |
|---|---|---|
| JP | S4922431 B | 6/1974 |
| JP | S5015993 U | 2/1975 |
| JP | S56151032 A | 11/1981 |
| JP | S6190648 A | 5/1986 |
| JP | S62109554 A | 5/1987 |
| JP | H03292939 A | 12/1991 |
| JP | 2007301070 A | 11/2007 |
| JP | 2009225904 A | 10/2009 |
| JP | 2010-022650 A | 2/2010 |
| JP | 2010022647 A | 2/2010 |
| JP | 2011508651 A | 3/2011 |
| WO | 2013119610 A1 | 8/2013 |

* cited by examiner

ULTRASONIC DIAGNOSING DEVICE

TECHNICAL FIELD

This disclosure relates to an ultrasonic diagnosing device, which diagnoses a state of a to-be-examined part based on echo signals caused by ultrasonic waves transmitted by a probe.

BACKGROUND ART

Conventionally, ultrasonic diagnosing devices for diagnosing a state of a to-be-examined part based on reflection echoes caused by ultrasonic waves transmitted to a to-be-examined part in a percutaneous manner, so as to analyze a state of the to-be-examined part that is an examination target in a to-be-examined body, are known. As such an ultrasonic diagnosing device, for example, Patent Document 1 discloses an ultrasonic probe supporting mechanism which supports an ultrasonic probe for transmitting ultrasonic waves via an acoustic matching member (ultrasonic wave penetrating part) having a curved shape along a kneecap (to-be-examined body), in a manner that the ultrasonic probe is movable along the to-be-examined body. With the ultrasonic probe supporting mechanism, the ultrasonic probe can suitably be positioned to measure a shape of a cartilage (to-be-examined part) of a knee joint, and the ultrasonic probe can suitably be moved along the to-be-examined body.

REFERENCE DOCUMENT OF CONVENTIONAL ART

Patent Document

Patent Document 1: JP2010-022647A

DESCRIPTION OF THE DISCLOSURE

Problems to be Solved by the Disclosure

Meanwhile, with the device described in Patent Document 1, the ultrasonic probe scans while being contact with a front surface of the ultrasonic wave penetrating part. Therefore, air bubbles may intervene between the probe and the front surface of the ultrasonic wave penetrating part. In such a case, a state between the probe and the ultrasonic wave penetrating part significantly varies, and thus, an intensity of the ultrasonic wave transmitted to the to-be-examined part by the probe may vary.

This disclosure is made in view of the above situations and aims to stabilize an intensity of an ultrasonic wave which reaches a to-be-examined part.

SUMMARY OF THE DISCLOSURE (1) In order to solve the subject described above, according to one aspect of the present disclosure, an ultrasonic diagnosing device for diagnosing a state of a to-be-examined part that is an examination target of a to-be-examined body, based on echo signals caused by ultrasonic signals transmitted to the to-be-examined part, is provided. The ultrasonic diagnosing device includes a container body containing liquid, an ultrasonic wave penetrating part having ultrasonic penetrability, covering an opening formed in the container body, and capable of coming in close contact with the to-be-examined body, a probe having an ultrasonic transmitting part configured to transmit the ultrasonic signals, the probe soaked in the liquid inside the container body in a state where the ultrasonic wave transmitting part is separated from the ultrasonic wave penetrating part, the ultrasonic signals transmitted to the to-be-examined part through the liquid and the ultrasonic wave penetrating part by the ultrasonic wave transmitting part, and a drive mechanism configured to move the probe soaked in the liquid inside the container body, and change a position of the ultrasonic wave transmitting part in a direction following a front surface shape of the to-be-examined part.

(2) The container body may have a to-be-examined body housing formed into a concave shape so that the to-be-examined body is capable of coming in close contact with the ultrasonic wave penetrating part when the to-be-examined body is received in the to-be-examined body housing.

(3) Moreover, the drive mechanism may include an electric motor having a rotatable output shaft extending in leftward-and-rightward directions of a knee received in the to-be-examined body housing, the knee being the to-be-examined body, and a rotary shaft having a swing shaft part extending in the extending direction of the output shaft and to which the probe is fixed, and a coupling part coupling the swing shaft part to the output shaft, the rotary shaft provided in the container body so that the probe fixed to the swing shaft part swings in a direction following a front surface shape of a cartilage of the knee received in the to-be-examined body housing, the cartilage being the to-be-examined part.

(4) Moreover, the rotary shaft may be formed with a communication hole configured to guide a cable connected with the probe to outside the container body.

(5) The drive mechanism may further include a slide mechanism configured to move the electric motor in the leftward-and-rightward directions of the knee received in the to-be-examined body housing.

(6) The to-be-examined body housing may be formed with a right kneecap housing section in which a right kneecap is received when the right knee is received in the to-be-examined body housing, and a left kneecap housing section in which a left kneecap is received when the left knee is received in the to-be-examined body housing.

(7) The drive mechanism may include a guiding part formed in one of a rail shape and a groove shape, extending in a direction following a front surface shape of a knee cartilage received in the to-be-examined body housing, the knee cartilage being the to-be-examined part, a probe holder having a guided part and configured to hold the probe, the guided part engaged with the guiding part and of which position is changeable along the guiding part, and a drive part configured to change the position of the probe holder along the guiding part.

(8) Moreover, the drive mechanism may further include a coupling part coupling the probe holder to the drive part by being coupled at one end side to the probe holder to be rotatable and being coupled at the other end side to the drive part.

Effects of the Disclosure

According to the present disclosure, an intensity of an ultrasonic wave which reaches a to-be-examined part can be stabilized.

MODES FOR CARRYING OUT THE DISCLOSURE

Figure 1:
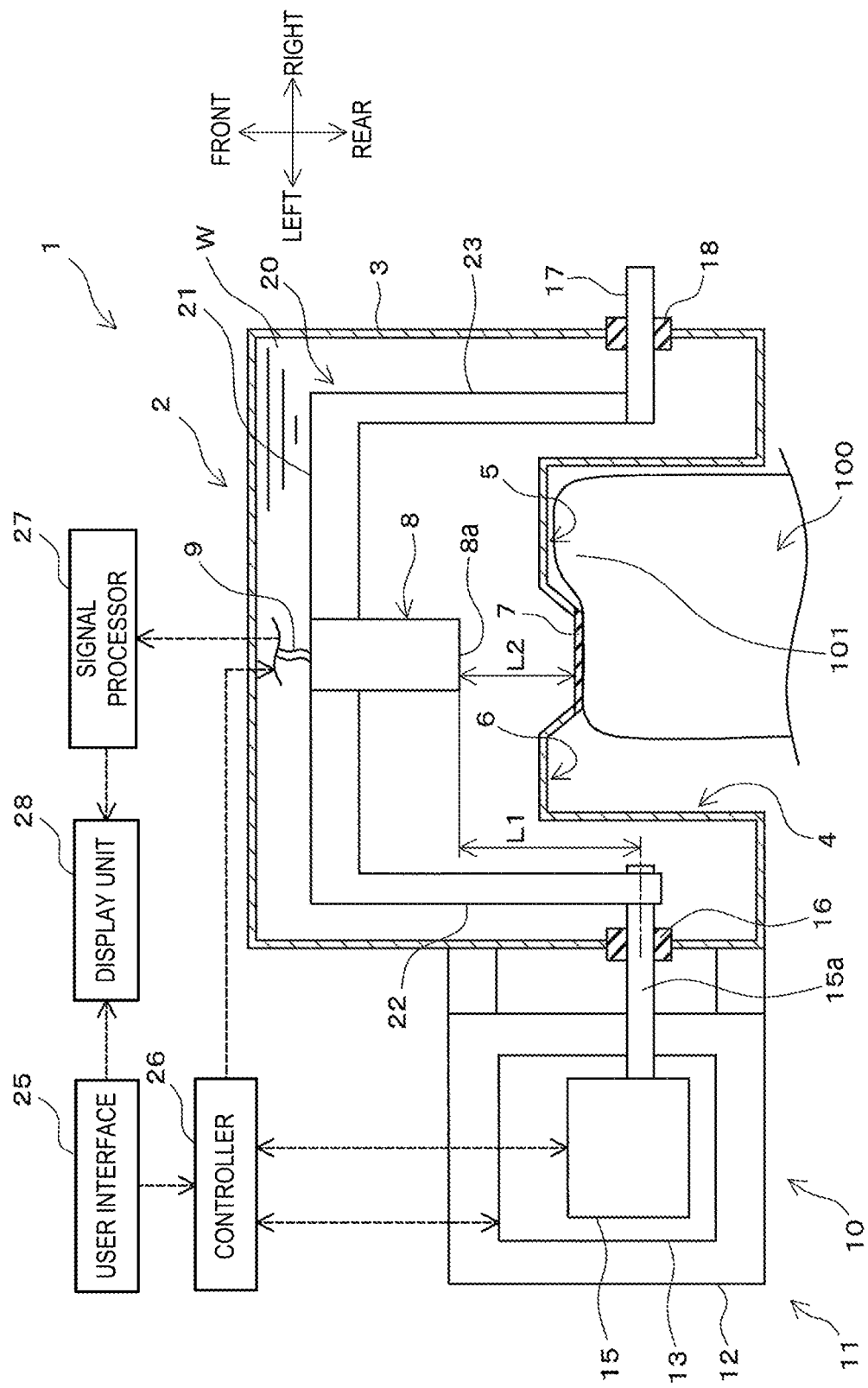
FIG. 1 is a schematic top view of an ultrasonic diagnosing device according to one embodiment of this disclosure, illustrating a state where a knee joint is set to the ultrasonic diagnosing device.
Figure 2:
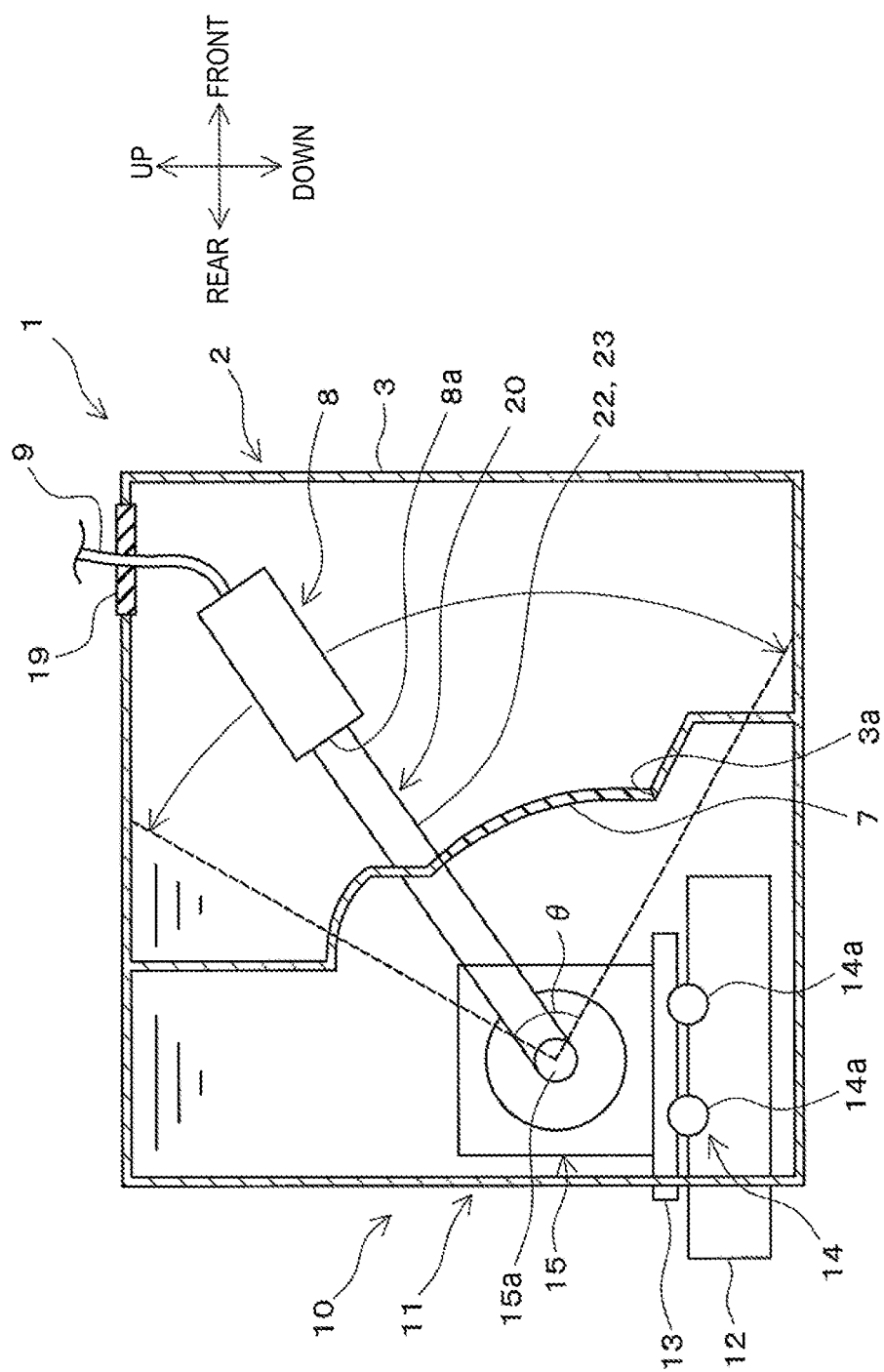
FIG. 2 is a schematic side view of the ultrasonic diagnosing device illustrated in FIG. 1.

An ultrasonic diagnosing device 1 according to one embodiment of this disclosure is described with reference to the drawings. FIG. 1 is a schematic top view of the ultrasonic diagnosing device 1, illustrating a state where a knee joint as a to-be-examined body is set to the ultrasonic diagnosing device 1. Further, FIG. 2 is a schematic side view of the ultrasonic diagnosing device 1.

With the ultrasonic diagnosing device 1 according to this embodiment, a medial condyle of femur in a knee joint cartilage (a to-be-examined part, hereinafter, may simply be referred to as the knee cartilage) is a diagnosis target. The knee cartilage generally has a curvature radius of about 30 mm to 40 mm in a side cross section thereof. The ultrasonic diagnosing device 1 according to this embodiment, although described later in detail, is configured so that a probe configured to transmit and receive ultrasonic signals performs an arc scan centering on a center of curvature of the knee cartilage, at a position separated from the knee cartilage. Thus, the probe changes its position in a direction following a shape of a front surface of the knee cartilage.

Note that, the arc scan is a scan in which the probe transmits ultrasonic signals toward inside of an arc while changing its position on the arc. Further in the following description, in the respective drawings, a direction indicated by the arrow noted as front is referred to as one of the front side and the forward direction, a direction indicated by the arrow noted as rear is referred to as one of the rear side and the rearward direction, a direction indicated by the arrow noted as up is referred to as one of the upper side and the upward direction, a direction indicated by the arrow noted as down is referred to as one of the lower side and the downward direction, a direction indicated by the arrow noted as right is referred to as one of the right side and the rightward direction, and a direction indicated by the arrow noted as left is referred to as one of the left side and the leftward direction, for the sake of convenience.

The ultrasonic diagnosing device 1 is configured to be capable of, in a state where a knee 100 (right knee or left knee) as the to-be-examined body is bent, transmitting ultrasonic signals from the front side of the knee to the knee cartilage (to-be-examined part), and diagnosing a state of the knee cartilage based on echo signals caused by the ultrasonic signals. Note that in FIG. 1, a state where the right knee 100 is set to the ultrasonic diagnosing device 1 is illustrated.

With the ultrasonic diagnosing device 1, the probe 8 configured to transmit the ultrasonic signals mechanically and automatically scans the knee cartilage in the direction following the front surface shape of the knee cartilage, and thus, echo signals from the knee cartilage within a requested range can be received. As illustrated in FIG. 1, the ultrasonic diagnosing device 1 includes a container 2, the probe 8, a drive mechanism 10, a user interface 25, a controller 26, a signal processor 27, and a display unit 28.

The container 2 contains water w that is liquid having ultrasonic penetrability. The container 2 has a container body 3 and a silicon sheet 7 covering an opening 3a formed in the container body 3.

As illustrated in FIGS. 1 and 2, the container body 3 is provided as a structural body in which liquid can be contained. In a rear part of the container body 3, a concave formed to concave in the forward direction and extending in the upward-and-downward directions is formed. The concave is provided as a knee housing 4 (to-be-examined body housing) in which the patient's knee 100 which is the diagnosis target is received.

In a right part of the knee housing 4, a concave formed to concave in the forward direction from a bottom part of the knee housing 4 and extending in the upward-and-downward directions is formed. The concave is provided as a right kneecap housing section 5 in which a cap of the patient's right knee is received. Further, in a left part of the knee housing 4, a concave formed to concave in the forward direction from the bottom part of the knee housing 4 and extending in the upward-and-downward directions is formed. The concave is provided as a left kneecap housing section 6 in which a cap of the patient's left knee is received.

The silicon sheet 7 is a sheet-shaped member made of silicon. The silicon sheet 7 is adhered to cover the opening 3a formed in a center portion of the bottom part of the knee housing 4 in the leftward-and-rightward directions, in other words, a portion between the right and left kneecap housing sections 5 and 6 in the knee housing 4. The silicon sheet 7 is provided as an ultrasonic wave penetrating part through which the ultrasonic wave transmitted by the probe 8 is penetrable. The opening 3a has, in a side view, a gentle curvature along the knee joint (e.g., about 60 mm).

Further, although the silicon sheet is used as the ultrasonic wave penetrating part in this embodiment, without limiting to this, any material may be used as long as it forms a member which can penetrate ultrasonic waves therethrough. Note that, it preferably is a member having elasticity to be in close contact with the patient's knee 100. Moreover in this embodiment, the silicon sheet 7 is directly adhered to the opening 3a; however, without limiting to this, it may be adhered via a member having a cushioning property and water resistance (e.g., closed cell foam rubber). Thus, a variation of degree of close contact between the patient's knee 100 and the silicon sheet 7 caused by difference in shape of the knee depending on the patient can be reduced.

The probe 8 is fixed to a rotary shaft 20 while soaked in the water w filling the container 2. More specifically, the probe 8 is fixed to the rotary shaft 20 so that an ultrasonic wave transmitting and receiving part 8a (ultrasonic wave transmitting part) that is a part configured to transmit and receive the ultrasonic signals, opposes to the silicon sheet 7 via the water w. The probe 8 is configured to transmit the ultrasonic signals to the patient's knee 100 received inside the knee housing 4, and receive echo signals caused by the transmitted ultrasonic signals.

The probe 8 is connected with the controller 26 and the signal processor 27 via a cable 9. As illustrated in FIG. 2, the cable 9 is guided outside the container 2 through an annular seal member 19 fitted into a cable hole formed in an upper wall of the container body 3. The ultrasonic wave transmitting and receiving part 8a of the probe 8 is configured to transmit the ultrasonic signals based on a command from the controller 26 and receive the echo signals caused by the ultrasonic signals. The echo signals received by the ultrasonic wave transmitting and receiving part 8a are suitably analyzed by the signal processor 27 to diagnose the state of the cartilage of the patient's knee 100.

The drive mechanism 10 causes the probe 8 soaked in the water w filling the container 2, to mechanically scan along the patient's knee. The drive mechanism 10 includes a main body 11 and the rotary shaft 20.

The main body 11 is disposed outside the container 2. The main body 11 has a pedestal 12, a slide part 13, a slide mechanism 14, and an electric motor 15.

A bottom face of the pedestal 12 is placed on an installation base etc., and thus, the main body 11 is set on the installation base. The pedestal 12 is formed into a substantially plate shape of which upper and lower faces are formed to be flat and having a given thickness in the upward-and-downward directions. The slide part 13 is disposed on the pedestal 12 via the slide mechanism 14.

The slide part 13 is provided as a separate member from the pedestal 12 and is disposed on the pedestal 12. In this embodiment, the slide part 13 is structured to be narrower than the pedestal 12 in a plan view and thinner than the pedestal 12 in the upward-and-downward directions, for example.

The slide mechanism 14 is provided between the pedestal 12 and the slide part 13, and slides the slide part 13 in the leftward-and-rightward directions with respect to the pedestal 12. The slide mechanism 14 has a plurality of slide rails 14a extending in the leftward-and-rightward directions, for example. The slide part 13 is in a state where it is slidable along the slide rails 14a in the leftward-and-rightward directions with respect to the pedestal 12.

The electric motor 15 is provided as a drive source configured to reciprocate the probe 8 fixed to the rotary shaft 20, within a given angle range θ (see FIG. 2). The electric motor 15 may be structured with a servomotor that is capable of an angle control, for example. The electric motor 15 changes a rotational position of the rotary shaft 20 based on a command from the controller 26.

The electric motor 15 has an output shaft 15a which is capable of rotating in both positive and negative directions. The output shaft 15a is provided to extend in the leftward-and-rightward directions of the knee 100 received in the knee housing 4. A tip part of the output shaft 15a is disposed inside the container body 3 via an annular seal member 16 fixedly inserted into a through hole formed in a side wall of the container body 3. The seal member 16 is provided as a water resistant slide part configured to hold the output shaft 15a to be rotatable with respect to the container 2 and prevent the water w inside the container 2 from leaking outside the container 2. The tip part (a part disposed inside the container body 3) of the output shaft 15a is fixed to one end side of the rotary shaft 20.

Further, the main body 11 has a slide actuator (not illustrated) that is a drive source configured to slide the slide part 13 with respect to the pedestal 12. The slide actuator changes the position of the slide part 13 in the leftward-and-rightward directions, based on a command from the controller 26.

The rotary shaft 20 has a swing shaft part 21 and a pair of crank parts 22 and 23, and these parts are integrally formed.

The swing shaft part 21 is a stick-shaped part provided to extend inside the container 2 in the extending direction of the output shaft 15a (the leftward-and-rightward directions of FIG. 1). As illustrated in FIGS. 1 and 2, the swing shaft part 21 is disposed in a part of space of the container 2, on the front side of the knee housing 4. In other words, the swing shaft part 21 is disposed on the front side of the knee 100 received in the knee housing 4, by being separated from the knee 100. The probe 8 is fixed to a center part of the swing shaft part 21 in the leftward-and-rightward directions, so that the ultrasonic wave transmitting and receiving part 8a opposes to the knee 100 via the water w and the silicon sheet 7.

The pair of crank parts 22 and 23 is connected at their respective one end portions with both end portions of the swing shaft part 21 so that they are perpendicular to the swing shaft part 21 and parallel to each other. One of the crank parts, the crank part 22 (the left crank part in FIG. 1), is fixed at its other end portion to the tip part of the output shaft 15a. In other words, the one of the crank parts, the crank part 22, is provided as a coupling part coupling the swing shaft part 21 to the output shaft 15a. The other crank part 23 (the right crank part in FIG. 1) is fixed at its other end portion to a supporting shaft 17. The supporting shaft 17 is provided to penetrate an annular seal member 18 fixedly inserted into a through hole formed in another side wall of the container body 3. The seal member 18 is provided, similar to the seal member 16, as a water resistant slide part configured to prevent the water w inside the container 2 from leaking outside the container 2.

With the configuration described above, the rotary shaft 20 is supported to be rotatable with respect to the container 2 via the output shaft 15a and the supporting shaft 17. Further, the rotary shaft 20 is actuated by the electric motor 15 to swing over the given angle range θ, and thus, the ultrasonic wave transmitting and receiving part 8a of the probe 8 swings over the given angle range θ along the front surface of the knee cartilage in the upward-and-downward directions.

Moreover, with the ultrasonic diagnosing device 1, a distance L1 from a wave transmitting surface of the ultrasonic wave transmitting and receiving part 8a to a center axis of the output shaft 15a, and a distance L2 from the wave transmitting surface to the silicon sheet 7 are determined based on a general thickness of a patient's soft tissue and a focal point of the probe 8.

The user interface 25 is comprised of a keyboard, a touch panel, etc., and receives an operational input from a user. In response to the operational input from the user, the user interface 25 commands the controller 26 to start transmitting and receiving the ultrasonic signals by the probe 8, and driving the drive mechanism 10 to cause the probe 8 to scan. Further, in response to the operational input from the user, the user interface 25 outputs a command to design or switch a display mode to the display unit 28. Note that the user interface 25 may be incorporated with the display unit 28.

The controller 26 generates the ultrasonic signals and outputs them to the probe 8. Further the controller 26 controls the electric motor 15 and the slide actuator to cause the probe 8 to scan a requested range of the knee 100.

The signal processor 27 analyzes the state of the knee cartilage based on the echo signals, and outputs the analysis result to the display unit 28. The display unit 28 displays the analysis result of the knee cartilage obtained by the signal processor 27. The user (e.g., doctor) looks at the analysis result displayed on the display unit 28 to diagnose the state of the patient's knee joint.

Usage of Ultrasonic Diagnosing Device

Next, a usage of the ultrasonic diagnosing device 1 according to this embodiment is described.

First, the patient's knee joint is set to the ultrasonic diagnosing device 1. Specifically, for example, in a case of diagnosing the joint of the patient's right knee 100, the right knee is received in the knee housing 4 so that an inner (medial condyle side) part of the right knee 100 comes in close contact with the silicon sheet 7. Here, a kneecap 101 of the right knee 100 is received in the right kneecap housing section 5. Thus, the right knee 100 can be set to the ultrasonic diagnosing device 1 without the kneecap contacting the container 2. Similarly, in a case of diagnosing the joint of the patient's left knee, the left knee is received in the knee housing 4 so that a kneecap of the left knee is received in the left kneecap housing section 6 and an inner part of the left knee comes in close contact with the silicon sheet 7.

After setting the patient's knee to the device 1 as described above, the user suitably controls the user interface 25. Thus, the controller 26 is activated to start the transmission and reception of the ultrasonic signals by the probe 8, and the electric motor 15 and the slide actuator are activated to cause the probe 8 to scan the given range of the patient's knee 100. Specifically, for example, in a state where the slide part 13 is located at a given position in the leftward-and-rightward directions, the controller 26 swings the rotary shaft 20 over the given angle range θ. Thus, the probe 8 can perform an arc scan at a certain position of the knee cartilage in the leftward-and-rightward directions. The arc scan is performed at a plurality of positions in the leftward-and-rightward directions of the knee cartilage, and thus, three-dimensional echo data along the cartilage front surface can be acquired. As the three-dimensional echo data, for example, echo data of which an X-axis is the leftward-and-rightward directions, a Y-axis is the upward-and-downward directions of the knee (the arc direction of the arc scan), and a Z-axis is an intensity of the echo signal, can be acquired.

When the probe 8 scans as described above (the scan in the leftward-and-rightward directions and the arc scan), the probe 8 changes its position while soaked in the water w inside the container 2. In other words, the ultrasonic wave transmitting and receiving part 8a does not come in contact with the silicon sheet 7 while moving. Conventionally, as disclosed in Patent Document 1 described above for example, the probe scans while being in contact with a front surface of an acoustic matching member (corresponding to the silicon sheet 7 of this embodiment). Thus, acquisition of an echo image requires comparatively long time. In this regard, with the ultrasonic diagnosing device 1, the ultrasonic signals are transmitted and received in a state where the water w with comparatively high ultrasonic penetrability intervenes between the ultrasonic wave transmitting and receiving part 8a and the silicon sheet 7, without the ultrasonic wave transmitting and receiving part 8a being in contact with the silicon sheet 7.

Moreover, the signal processor 27 analyzes the state of the knee cartilage based on the three-dimensional echo data acquired as described above, and outputs the analysis result to the display unit 28. The user can diagnose the state of the knee cartilage by looking at the analysis result displayed on the display unit 28. Note that the signal processor 27 may be configured to generate an echo image based on the three-dimensional echo data and display the echo image on the display unit 28. In this case, the user can diagnose the state of the patient's knee cartilage by looking at the echo image displayed on the display unit 28.

Effects

As described above, with the ultrasonic diagnosing device 1 according to this embodiment, the ultrasonic wave transmitting and receiving part 8a scans the knee 100 while transmitting and receiving the ultrasonic waves through the water w, to the ultrasonic wave penetrating part (silicon sheet 7) which is in close contact with the knee 100. In other words, with the ultrasonic diagnosing device 1, there is no possibility of air bubbles entering between the ultrasonic wave transmitting and receiving part 8a and the silicon sheet 7, and a state between the ultrasonic wave transmitting and receiving part 8a and the silicon sheet 7 does not significantly vary. Thus, a variation of an intensity of an ultrasonic wave which reaches the knee cartilage front surface is reduced.

Therefore, with the ultrasonic diagnosing device 1, the intensity of the ultrasonic wave which reaches the knee cartilage as the to-be-examined part can be stabilized, and thus, reliability of the device can be improved.

Further, with the ultrasonic diagnosing device 1, the drive mechanism 10 moves the probe 8 so that the ultrasonic wave transmitting and receiving part 8a changes its position in the direction following the front surface shape of the knee cartilage. Thus, the probe 8 can scan while keeping a substantially fixed distance between the ultrasonic wave transmitting and receiving part 8a and the front surface of the knee cartilage. As a result, an accurate echo image of the knee cartilage can be obtained.

Further, with the ultrasonic diagnosing device 1, since the knee housing 4 where the knee 100 as the to-be-examined body is received is formed in the container 2, the knee 100 can be diagnosed by the knee 100 being suitably set to the device 1.

Further, with the ultrasonic diagnosing device 1, the rotary shaft 20 to which the probe 8 is fixed is swung by the electric motor 15, and thus, the probe 8 can be moved in the direction following the front surface shape of the knee cartilage.

Further, with the ultrasonic diagnosing device 1, the output shaft 15a of the electric motor 15 is provided to extend in the leftward-and-rightward directions of the knee 100 received in the knee housing 4. Moreover, the ultrasonic diagnosing device 1 includes the rotary shaft 20 in which the swing shaft part 21 provided to extend in the extending direction of the output shaft 15a at the position on the front side of the knee 100 which is received in the knee housing 4 is integrally formed with the crank part 22 coupling the swing shaft part 21 to the output shaft 15a. With this configuration, when the output shaft 15a is rotated, the swing shaft part 21 moves along an arc with a comparatively large curvature radius by following the front surface shape of the knee cartilage, on the front side of the knee 100. Therefore, according to the ultrasonic diagnosing device 1, the configuration with which the probe 8 is moved in the direction following the front surface shape of the knee cartilage can suitably be achieved with a comparatively simple configuration including the electric motor 15 and the rotary shaft 20.

Further, with the ultrasonic diagnosing device 1, since the slide mechanism 14 can move the electric motor 15 in the leftward-and-rightward directions, the probe 8 can scan in the leftward-and-rightward directions of the knee cartilage. Moreover, with the ultrasonic diagnosing device 1, the controller 26 can activate the electric motor 15 configured to cause the probe 8 to perform the arc scan, and the slide actuator configured to cause the probe 8 to scan in the leftward-and-rightward directions of the knee 100. Thus, for example, the three-dimensional echo data of which the X-axis is the leftward-and-rightward directions of the knee, the Y-axis is the upward-and-downward directions of the knee (the arc direction of the arc scan), and the Z-axis is the intensity of the echo signal, can automatically be acquired.

Further, with the ultrasonic diagnosing device 1, since the right and left kneecap housing sections 5 and 6 are provided, both of the right and left knee cartilages can suitably be set to the device 1.

Although the embodiment of this disclosure is described above, this disclosure is not limited to the above, and without deviating from the scope of this disclosure, various modifications may be applied.

Figure 3:
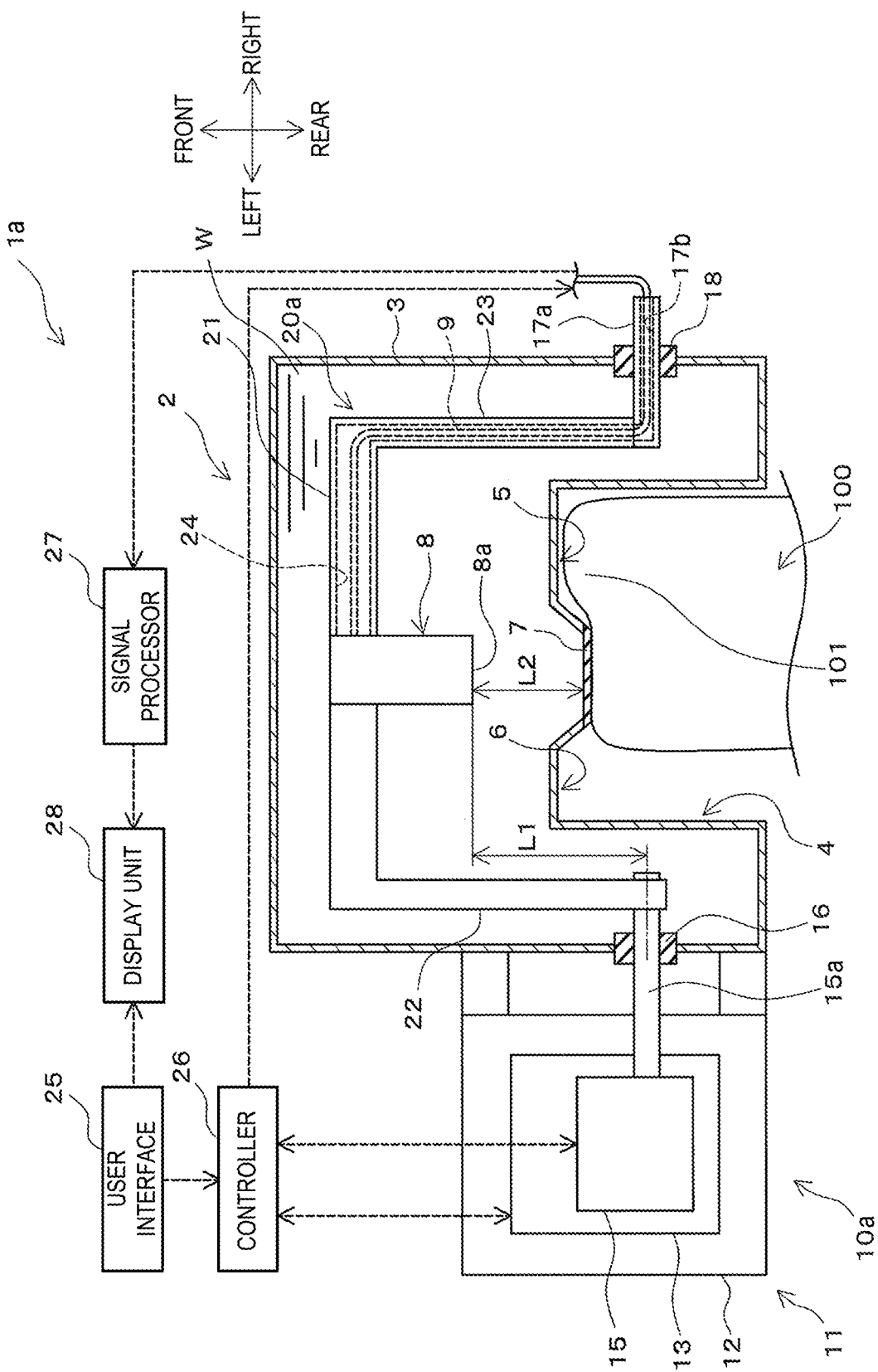
FIG. 3 is a schematic top view of an ultrasonic diagnosing device according to a modification, illustrating a state corresponding to FIG. 1.

Modifications (1) FIG. 3 is a schematic top view of an ultrasonic diagnosing device 1a according to a modification, illustrating a state corresponding to FIG. 1. The configuration of the ultrasonic diagnosing device 1a according to this modification is mainly different from the above embodiment in terms of a configuration of a drive mechanism 10a, particularly configurations of a rotary shaft 20a and a supporting shaft 17a.

As illustrated in FIG. 3, the rotary shaft 20a of this modification is formed with a through hole from a part where the probe 8 is fixed, to a part on the supporting shaft 17a side. The through hole is formed as a communication hole 24 which guides the cable 9 connected with the probe 8 to outside the container 2. The communication hole 24 is communicated with the outside of the container 2 through a through hole 17b formed in the supporting shaft 17a.

Further, in this modification, the cable 9 connected with the probe 8 is guided outside the container 2 through the communication hole 24 and the through hole 17b described above. Thus, with the ultrasonic diagnosing device 1a according to this modification, different from the case of the above embodiment, the cable hole through which the cable 9 penetrates the container 2 and the seal member 19 which prevents the water leakage between the cable 9 and the cable hole can be omitted.

Figure 4:
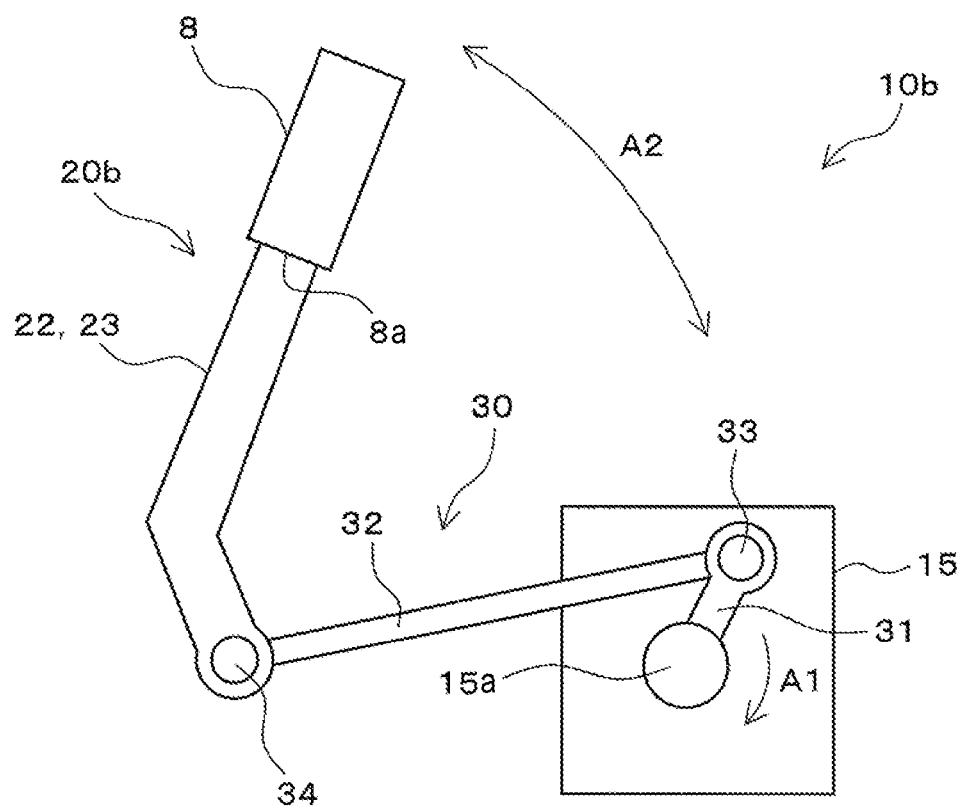
FIG. 4 is a schematic view of a drive mechanism of an ultrasonic diagnosing device according to another modification.

(2) FIG. 4 is a schematic view of a drive mechanism 10b of an ultrasonic diagnosing device according to another modification. The ultrasonic diagnosing device according to this modification is greatly different from the above embodiment in terms of a configuration of the drive mechanism 10b.

As illustrated in FIG. 4, the drive mechanism 10b of this modification has a link mechanism 30. The link mechanism 30 has a first link member 31 and a second link member 32 respectively having a substantially straight shape.

The first link member 31 is formed into a comparatively short rod shape. The first link member 31 is fixed at one end side to the output shaft 15a of the electric motor 15 so that an axial direction of the first link member 31 becomes perpendicular to the axial direction of the output shaft 15a. On the other hand, the first link member 31 is fixed at the other end side to one end side of the second link member 32 by a coupling pin 33 so as to be swingable.

The second link member 32 is formed into a rod shape longer than the first link member 31. The second link member 32 is fixed at the end side to the other end side of the first link member 31 by the coupling pin 33 so as to be swingable, as described above. On the other hand, the second link member 32 is fixed at the other end side to a rotary shaft 20b by a coupling pin 34 so as to be swingable.

Similar to the case of the above embodiment, the rotary shaft 20b has the swing shaft part 21 and the pair of crank parts 22 and 23, and these parts are integrally formed. The pair of crank parts 22 and 23 respectively has a bent portion at an intermediate position in the extending direction of the crank parts 22 and 23.

The electric motor 15 of this modification can be structured with a motor having the output shaft 15a rotatable only in one direction. In other words, by providing the link mechanism 30 described above, even without using the motor rotatable in both positive and negative directions, by rotating the output shaft 15a only in the one direction (the arrow A1 in FIG. 4), the probe 8 can be swung along the arrows A2 in FIG. 4. Note that, to detect an angular position of the probe 8 by the ultrasonic diagnosing device according to this modification, a rotary encoder (not illustrated) configured to detect a rotational position of the rotary shaft 20b may be used.

Further, also with the ultrasonic diagnosing device according to this modification, similar to the case of the above embodiment, the arc scan by the probe 8 can be performed without being in contact with the silicon sheet 7 as the ultrasonic wave penetrating part. Thus, it can be prevented that air bubbles enter between the ultrasonic wave transmitting and receiving part 8a and the silicon sheet 7, and as a result, similar to the case of the above embodiment, the intensity of the ultrasonic wave which reaches the knee cartilage as the to-be-examined part can be stabilized and the reliability of the device can be improved.

Figure 5:
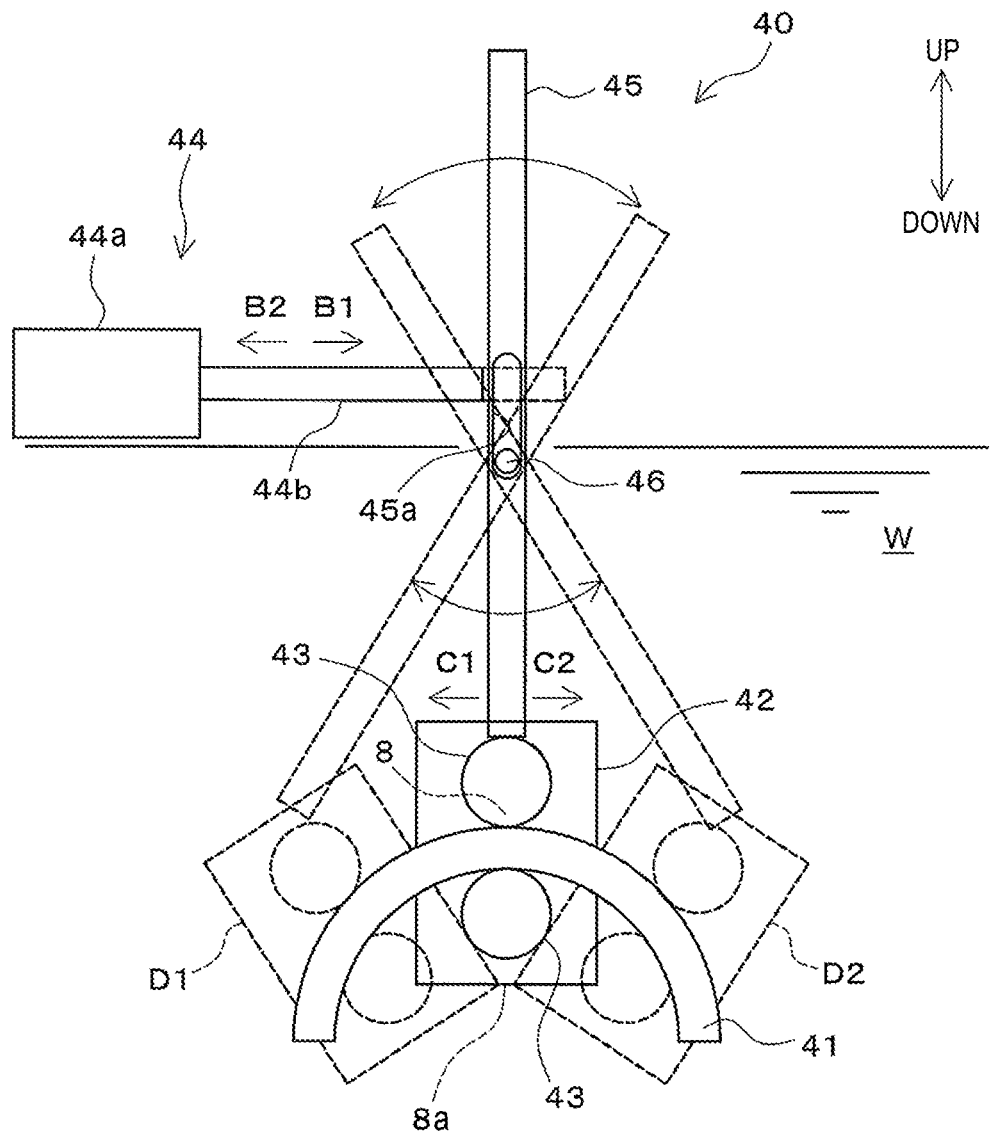
FIG. 5 is a schematic view of a drive mechanism of an ultrasonic diagnosing device according to another modification.
Figure 6:
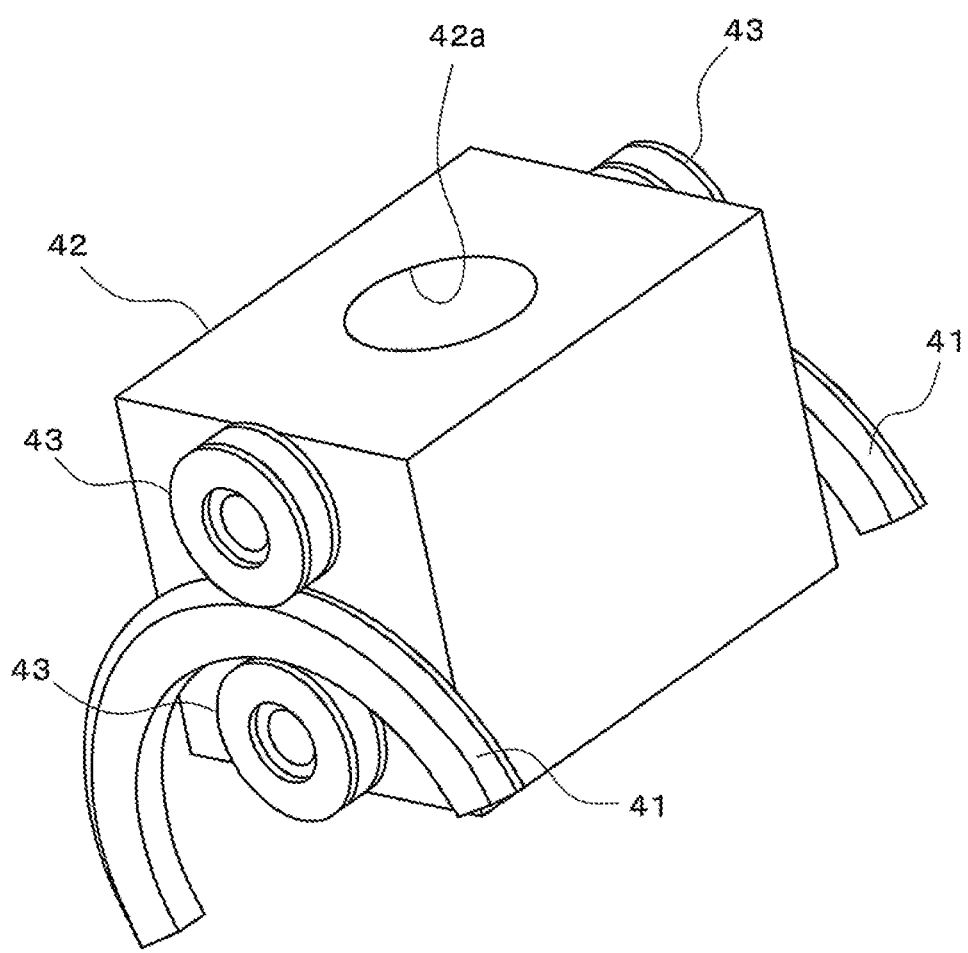
FIG. 6 is a perspective view illustrating part of the drive mechanism illustrated in FIG. 5, in an enlarged manner.

(3) FIG. 5 is a schematic view of a drive mechanism 40 of an ultrasonic diagnosing device according to another modification. Further, FIG. 6 is a perspective view illustrating part of the drive mechanism 40 in an enlarged manner. The ultrasonic diagnosing device according to this modification is greatly different from the above embodiment in terms of a configuration of the drive mechanism 40. More specifically, the drive mechanism 40 of this modification is configured such that the probe 8 changes its position along a requested track by moving along rail parts 41. As illustrated in FIGS. 5 and 6, the drive mechanism 40 includes a pair of rail parts 41, a probe holder 42, a pair of guide rollers 43 provided for each rail part 41, a linear actuator 44 (drive part), and a coupling part 45.

The pair of rail parts 41 is provided as guiding parts formed in a rail shape extending in the direction following the front surface shape of the knee cartilage. The pair of rail parts 41 is respectively structured with a stick-shaped member extending in an arc shape. Specifically, for example, the rail parts 41 are formed in an arc shape centering on the center of curvature of the cartilage of the knee 100 received in the knee housing 4, and disposed by being separated to the front side from the knee 100. Although the illustration is omitted, the pair of rail parts 41 is fixed to the container body 3 so as to be separated from each other and overlap in a plan view.

The probe holder 42 is structured with a block-shaped member. The probe holder 42 is formed with a probe insertion hole 42a through which the probe 8 is inserted and fixed. The probe holder 42 is sandwiched between the pair of rail parts 41.

To the probe holder 42, two pairs of guide rollers 43 are attached to be rotatable with respect to the probe holder 42. The pairs of guide rollers 43 are provided as guided parts engaged with the rail parts 41 and capable of changing positions along the rail parts 41, respectively. Each pair of guide rollers 43 holds the corresponding rail part 41 by sandwiching the rail part 41 therebetween. Thus, the probe holder 42 is changeable of its position along the pair of rail parts 41 via the guide rollers 43.

The linear actuator 44 is configured such that a rod part 44b moves in projecting and retreating directions with respect to a main body 44a. The linear actuator 44 is disposed on the upper side of the water w inside the container 2 so that the rod part 44b extends in a horizontal direction. The rod part 44b elongates and contracts in the horizontal direction. A tip portion of the rod part 44b is coupled to one end side of the coupling part 45.

The coupling part 45 is structured with a straight stick-shaped member coupling the tip portion of the rod part 44b to a rear end portion of the probe holder 42 (a portion on an opposite side from the ultrasonic wave transmitting and receiving part 8a of the probe 8 which is held by the probe holder 42). The coupling part 45 is coupled at the end side (rod part 44b side) portion to the tip portion of the rod part 44b so that the tip portion of the rod part 44b becomes slidable in the extending direction of the coupling part 45. On the other hand, the other end side (probe holder 42 side) of the coupling part 45 is coupled to the probe holder 42 so as to be rotatable with respect to the probe holder 42.

A hole 45a is formed in the coupling part 45, between the portion coupled to the rod part 44b and the portion coupled to the probe holder 42. The hole 45a penetrates the coupling part 45 in a direction perpendicular to the extending direction of the coupling part 45 and formed into an elongate hole in the extending direction of the coupling part 45. Further, a fulcrum shaft 46 fixed to the container 2 is inserted through the hole 45a. Thus, the coupling part 45 is supported by the fulcrum shaft 46 to be swingable.

With the ultrasonic diagnosing device according to this modification, when the probe 8 performs the arc scan, the rod part 44b of the linear actuator 44 may be moved in the projecting and retreating directions with respect to the main body 44a.

When the rod part 44b is moved in the projecting direction with respect to the main body 44a (a direction of the arrow B1 in FIG. 5), the rod part 44b pushes the coupling part 45, at a portion on the upper side of the fulcrum shaft 46. Here, a force acts on a portion of the coupling part 45 on the lower side of the fulcrum shaft 46, in a direction of the arrow C1 by having the fulcrum shaft 46 as a fulcrum. Accordingly, the pairs of guide rollers 43 move to the arrow C1 side while sandwiching the rail parts 41 therebetween, respectively. As a result, the probe holder 42 to which the pairs of guide rollers 43 are attached also moves to the C1 side, and thus, the position of the probe holder 42, in other words the probe 8, can be changed to a position D1 along the rail parts 41.

On the other hand, when the rod part 44b is moved in the retreating direction with respect to the main body 44a (a direction of the arrow B2 in FIG. 5), the rod part 44b pulls the coupling part 45, at the portion on the upper side of the fulcrum shaft 46. Here, a force acts on the portion of the coupling part 45 on the lower side of the fulcrum shaft 46, in a direction of the arrow C2 by having the fulcrum shaft 46 as a fulcrum. Accordingly, the pairs of guide rollers 43 move to the arrow C2 side while sandwiching the rail parts 41 therebetween, respectively. As a result, the probe holder 42 to which the pairs of guide rollers 43 are attached also moves to the C2 side, and thus, the position of the probe holder 42, in other words the probe 8, can be changed to a position D2 along the rail parts 41.

Also with the ultrasonic diagnosing device according to this modification, similar to the case of the above embodiment, the arc scan by the probe 8 can be performed without being in contact with the silicon sheet 7 as the ultrasonic wave penetrating part, and therefore, it can be prevented that air bubbles enter between the ultrasonic wave transmitting and receiving part 8a and the silicon sheet 7, and as a result, the intensity of the ultrasonic wave which reaches the knee cartilage can be stabilized.

Note that in this modification, the guiding parts are structured with the rail parts 41, and the guided parts are structured with the guide rollers 43; however it is not limited to this. Specifically, for example, the guiding parts may be structured with grooves formed along the rail parts, and the guided parts may be structured with protrusions protruding from the probe holder, engaged with the grooves, and capable of sliding along the grooves, respectively.

Figure 7:
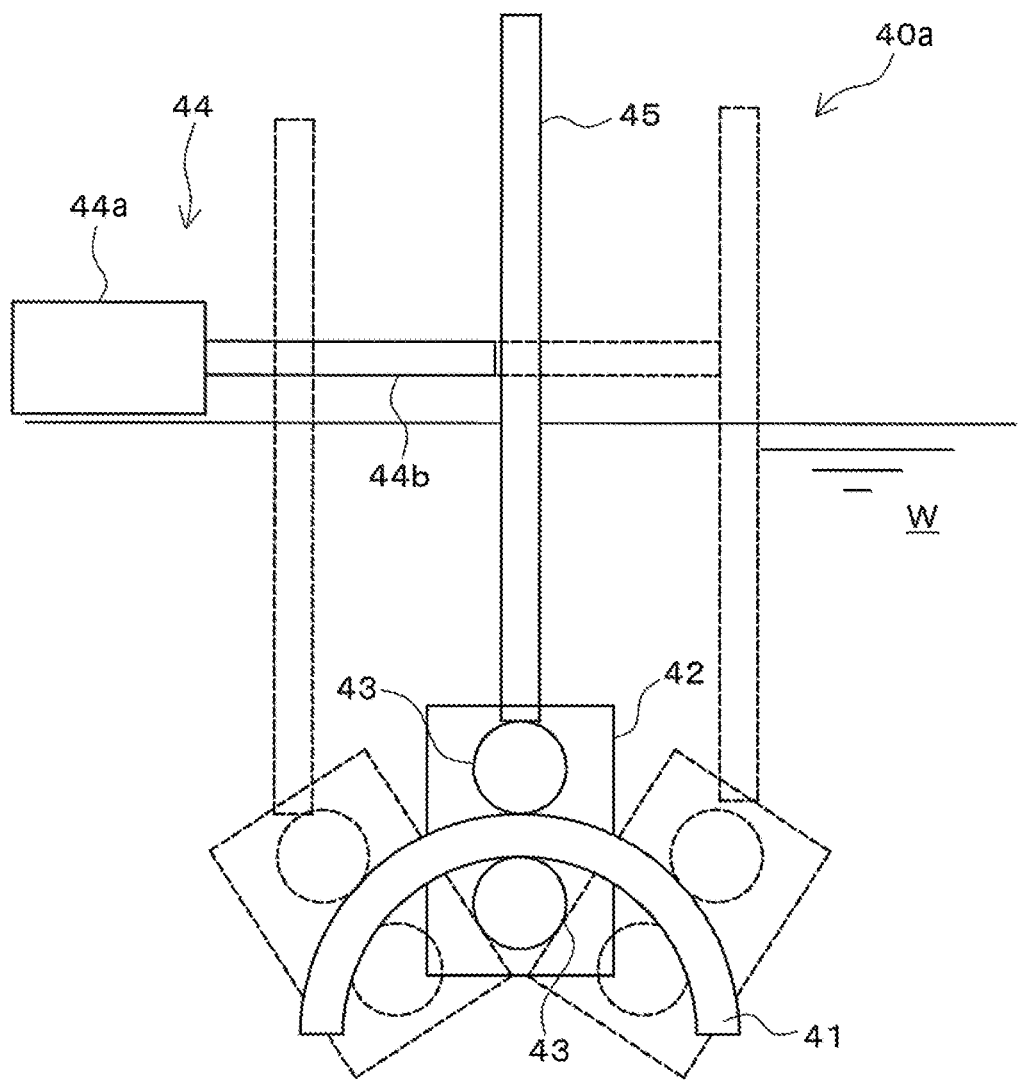
FIG. 7 is a schematic view of a drive mechanism of an ultrasonic diagnosing device according to another modification, illustrating a state corresponding to FIG. 5.

(4) FIG. 7 is a schematic view of a drive mechanism 40a of an ultrasonic diagnosing device according to another modification. The drive mechanism 40a of the ultrasonic diagnosing device according to this modification has a similar structure to the drive mechanism 40 illustrated in FIG. 5. Specifically, similar to the drive mechanism 40 illustrated in FIG. 5, the drive mechanism 40a according to this modification includes the pair of rail parts 41, the probe holder 42, the pairs of guide rollers 43 provided for the respective rail parts 41, the linear actuator 44 (drive part), and the coupling part 45. However, different from the drive mechanism 40 illustrated in FIG. 5, the drive mechanism 40a is not formed with the hole 45a in the coupling part 45, and is configured such that the coupling part 45 slides in the in the projecting and retreating directions of the rod part 44b. Even with such a configuration, the probe 8 can perform the arc scan.

Figure 8:
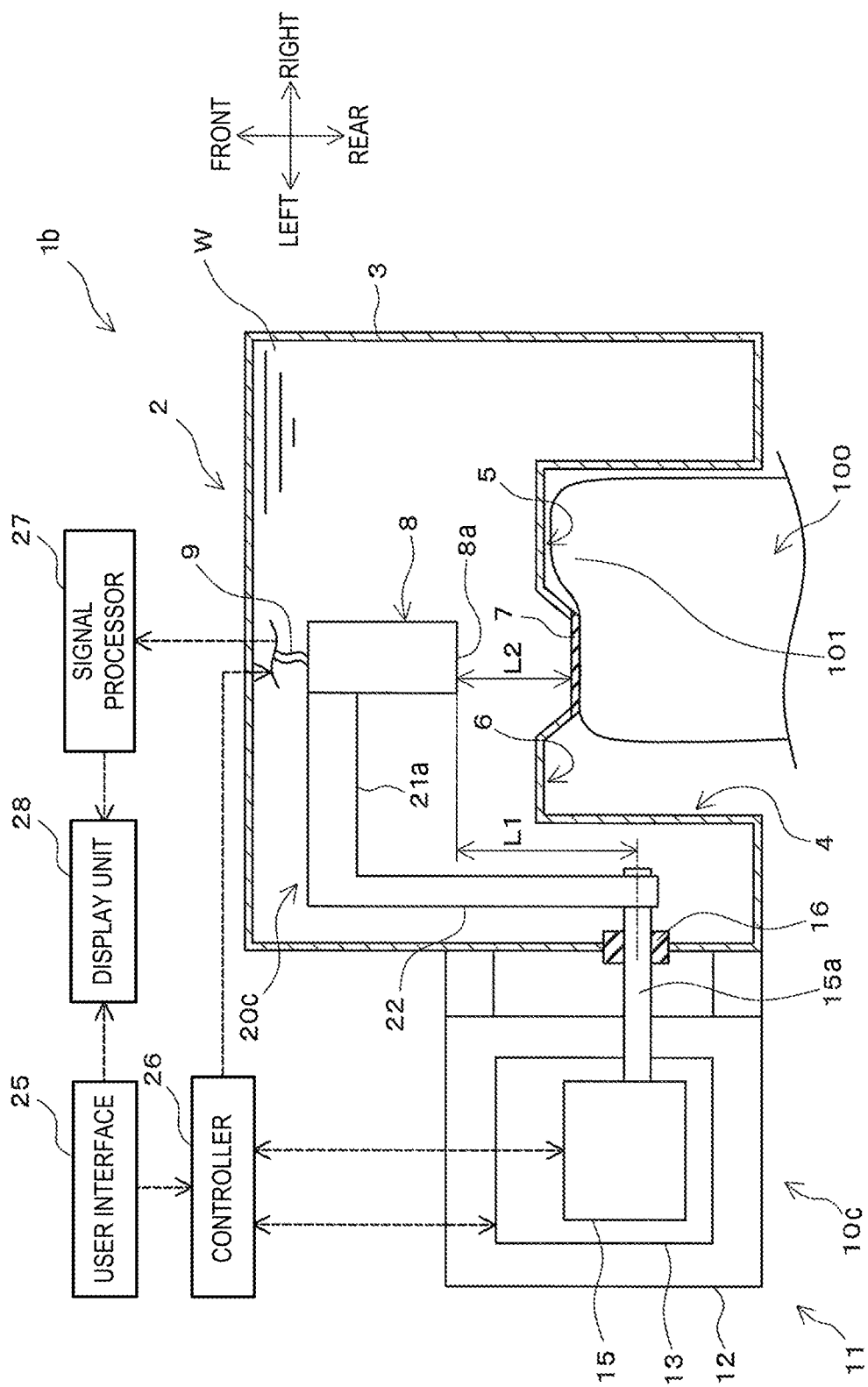
FIG. 8 is a schematic top view of an ultrasonic diagnosing device according to another modification, illustrating a state corresponding to FIG. 1.

(5) FIG. 8 is a schematic view of an ultrasonic diagnosing device 1b according to another modification, illustrating a state corresponding to FIG. 1. In the above embodiment, the rotary shaft 20 is supported to the container 2 via the output shaft 15a and the supporting shaft 17; however, it is not limited to this. Specifically, as illustrated in FIG. 8, a rotary shaft 20c may be supported to the container 2 only via the output shaft 15a. Thus, compared to the above embodiment, part of the rotary shaft, the supporting shaft 17, the seal member 18, etc. can be omitted. As a result, the structure of the device can be simplified.

(6) In the above embodiment, the controller 26 controls the electric motor 15 and the slide actuator to acquire the three-dimensional echo data along the cartilage front surface; however, it is not limited to this. For example, a configuration may be provided in which the controller 26 is capable of controlling only the electric motor 15. In this case, the slide part 13 is manually slid and the electric motor 15 is activated while fixed to a given position in the leftward-and-rightward directions. Thus, the arc scan can be performed. Therefore, the arc scan can be performed on a requested position of the knee 100 in the leftward-and-rightward directions without moving the knee 100 received in the knee housing 4 in the leftward-and-rightward directions. In addition, with this configuration, the slide actuator can be omitted, and thus, the structure of the device can be simplified.

DESCRIPTION OF REFERENCE NUMERALS 1, 1a, 1b Ultrasonic Diagnosing Device
3 Container Body
3a Opening
7 Silicon Sheet (Ultrasonic Wave Penetrating Part)
8 Probe
8a Ultrasonic Wave Transmitting and Receiving Part (Ultrasonic Wave Transmitting Part)
10, 10a, 10b, 10c, 40, 40a Drive Mechanism 100 Knee (To-be-examined Body)
w Water (Liquid)

What is claimed is:

1. An ultrasonic diagnosing device for diagnosing a state of a knee, based on echo signals caused by ultrasonic signals configured to be transmitted to the knee, comprising:
   a container body containing liquid;
   an ultrasonic wave penetrable cover, covering an opening formed in the container body, and capable of, via elasticity, forming a curvature having a first portion in contact with a medial condyle side part of the knee and a second portion proximate and spaced apart from a right kneecap or a left kneecap of the knee;
   a probe having an ultrasonic wave transmitter configured to transmit the ultrasonic signals, the probe immersed in the liquid inside the container body in a state where the ultrasonic wave transmitter is separated by a distance from the ultrasonic wave penetrable cover and opposes the ultrasonic wave penetrable cover, the ultrasonic signals configured to be transmitted to the knee through the liquid and the first portion of the ultrasonic wave penetrable cover by the ultrasonic wave transmitter; and
   a drive motor configured to move the probe immersed in the liquid inside the container body, and further configured to change a position of the ultrasonic wave transmitter in a direction following a front surface shape of a cartilage of the knee,
   wherein the container body has a housing formed to include a concavity and the ultrasonic wave penetrable cover is provided on a surface of the concavity that extends into a void of the concavity in a transmission direction of the ultrasonic signals further than a recessed adjacent surface of the concavity, so that the first portion of the ultrasonic wave penetrable cover is capable of contacting the medial condyle side part of the knee when the knee is received in the concavity of the housing, and so that the recessed adjacent surface accommodates another portion of the knee when the knee is received in the housing,
   wherein the housing is formed with a right kneecap housing section in which the right kneecap is received when a right knee is received in the housing, and a left kneecap housing section in which the left kneecap is received when a left knee is received in the housing, the recessed adjacent surface forming a portion of one of the right kneecap housing section and the left kneecap housing section.

2. The ultrasonic diagnosing device of claim 1, wherein the drive motor includes:
   an electric motor having a rotatable output shaft extending in leftward-and-rightward directions of the knee received in the housing; and
   a rotary shaft having a swing shaft part extending in an extending direction of the output shaft and to which the probe is fixed, and a coupling part coupling the swing shaft part to the output shaft, the rotary shaft provided in the container body so that the probe fixed to the swing shaft part swings in the direction following the front surface shape of the cartilage of the knee received in the housing.

3. The ultrasonic diagnosing device of claim 2, wherein the rotary shaft is formed with a communication hole configured to guide a cable connected with the probe to outside the container body.

4. The ultrasonic diagnosing device of claim 2, wherein the drive motor further includes a slide mechanism configured to move the electric motor in the leftward-and-rightward directions of the knee received in the housing.

5. The ultrasonic diagnosing device of claim 1, wherein the drive motor includes:
   one of a rail and a groove, extending in the direction following the front surface shape of the knee received in the housing; a probe holding block having guide rollers and configured to hold the probe, the guide rollers engaged with the guiding rail and of which position is changeable along the guiding rail;
   and a drive actuator configured to change the position of the probe holding block along the guiding rail.

6. The ultrasonic diagnosing device of claim 5, wherein the drive motor further includes a coupling part coupling the probe holding block to the drive actuator by being coupled at one end side to the probe holding block to be rotatable and being coupled at the other end side to the drive actuator.

7. The ultrasonic diagnosing device of claim 1, wherein the distance separating the ultrasonic wave transmitter from the ultrasonic wave penetrable cover is determined at least in part based on a focal point of the probe.

8. The ultrasonic diagnosing device of claim 7, wherein the distance separating the ultrasonic wave transmitter from the ultrasonic wave penetrable cover is determined further based on a thickness of soft tissue of the knee.

* * * * *